United States Patent [19]

Sorich

[11] Patent Number: 4,515,583
[45] Date of Patent: May 7, 1985

[54] OPERATIVE ELLIPTICAL PROBE FOR ULTRASONIC SURGICAL INSTRUMENT AND METHOD OF ITS USE

[75] Inventor: Richard A. Sorich, Santa Ana, Calif.
[73] Assignee: CooperVision, Inc., Menlo Park, Calif.
[21] Appl. No.: 542,435
[22] Filed: Oct. 17, 1983
[51] Int. Cl.³ .............................................. A61B 17/20
[52] U.S. Cl. .................... 604/22; 128/305; 604/239; 604/51
[58] Field of Search ............... 128/24 A, 303 C, 305, 128/339; 604/22, 118, 119, 239, 272, 46, 48, 51; 433/118, 119; 30/272, 316

[56] References Cited

U.S. PATENT DOCUMENTS

| | | |
|---|---|---|
| 1,331,271 | 2/1920 | Mac Gregor . |
| 2,774,193 | 12/1956 | Thatcher et al. ..................... 51/59 |
| 3,589,363 | 6/1971 | Banko et al. ........................ 128/276 |
| 3,693,613 | 9/1972 | Kelman ............................. 128/24 A |
| 3,805,787 | 4/1974 | Banko ................................ 128/276 |
| 4,236,510 | 12/1980 | Hatter et al. ...................... 128/24 A |
| 4,320,761 | 3/1982 | Haddad .............................. 604/22 |

Primary Examiner—Stephen C. Pellegrino
Assistant Examiner—J. L. Kruter
Attorney, Agent, or Firm—Vorys, Sater, Seymour and Pease

[57] ABSTRACT

An improved ultrasonic surgical aspirator for use in breaking up and removing tissue from an operative site recessed within a tissue body employs an elongated probe having an oval or elliptical cross section to more closely conform to and fit an incision in the tissue and to expose a wider area of tissue to ultrasonic vibrations as the operative tip of the probe is moved over the tissue. An improved method of performing a lensectomy on the human eye using the improved apparatus is also disclosed.

15 Claims, 7 Drawing Figures

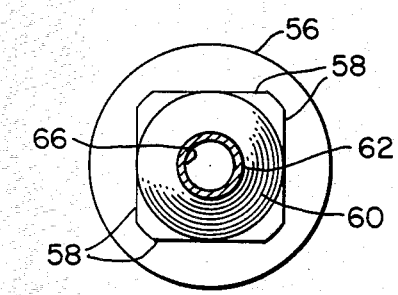
FIG. 3.
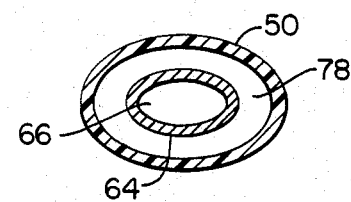
FIG. 4.
FIG. 5.
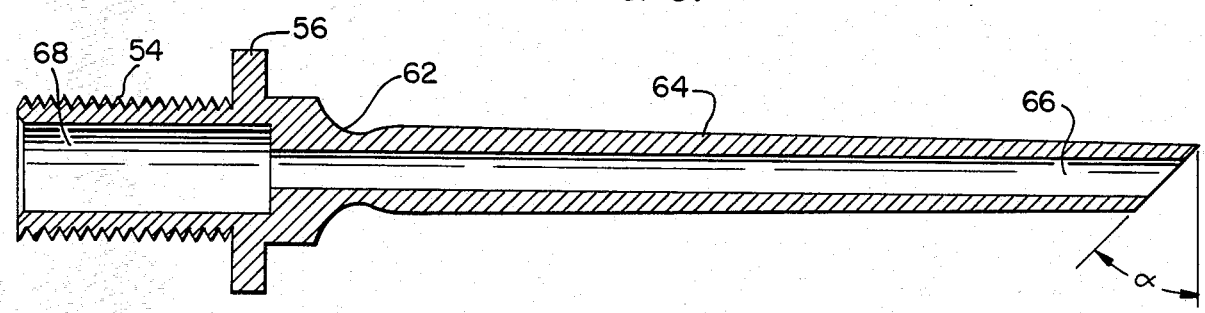
FIG. 7.
FIG. 6.
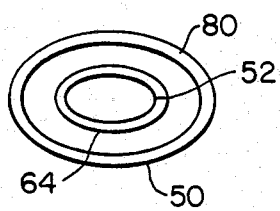
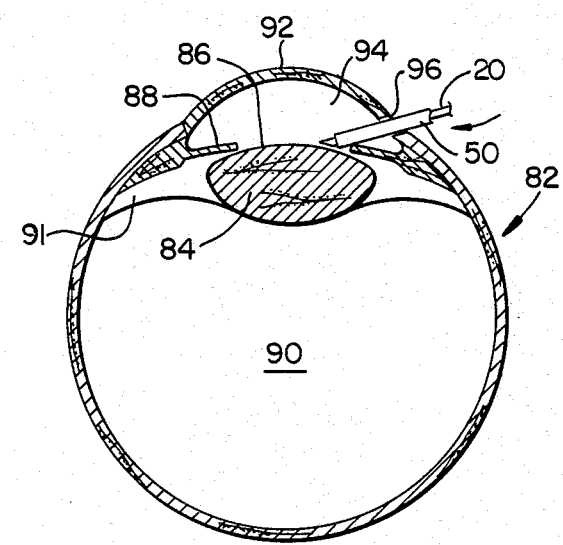

OPERATIVE ELLIPTICAL PROBE FOR ULTRASONIC SURGICAL INSTRUMENT AND METHOD OF ITS USE

BACKGROUND OF THE INVENTION

1. Field of the Invention

This invention relates to surgical instruments of the type which employs ultrasonic energy for operating on tissue and more particularly to an improved operative probe for use on such instruments to remove tissue from within a body and to the method of removing tissue from a body by use of such improved instruments.

2. Description of the Prior Art

Surgical instruments utilizing ultrasonic vibrations in combination with the circulation of irrigation liquid over the operative site for the removal of tissue from a biological body are well known and widely used particularly in enclosed or substantially enclosed operative sites. Such surgical instruments are particularly well adapted for use in the removal of cataracts and specific reference to such use will be made herein although it should be understood that the surgical instruments may be used for various other operative procedures.

The known ultrasonic surgical instruments of the type with which the present invention is concerned are frequently referred to as ultrasonic aspirators and conventionally employ an elongated probe or operative tip having one end rigidly attached through a vibration transmission member to a transducer for supplying ultrasonic energy to the other or free end of the probe where the ultrasonic energy is emitted to dislodge and break up or emulsify tissue for removal by aspiration. Irrigating fluid is delivered through a shield, or sheath surrounding the body of the probe for discharge adjacent to the tip or free end of the probe and returned by suction through the hollow center of the tubular body of the probe. An ultrasonic surgical aspirator of this type is disclosed in U.S. Pat. No. 3,805,787 and includes conduits for applying suction through the center of the vibration transmitting operative probe and for supplying irrigating fluid around the outer surface of the probe through a passage defined by a tubular shield. The irrigation fluid flows around the free end of the probe element and back through the center of the probe to effectively irrigate and remove dislodged and emulsified tissue. Various shield arrangements for controlling or directing the flow or irrigating fluid in the vicinity of the free end of the operative probe may be provided in accordance with this prior patent, and U.S. Pat. No. 3,693,316 discloses a flow control system for avoiding the application of excessive pressure or suction at the operative site.

The known ultrasonic aspirators have employed an elongated tubular vibration transmitting body having means such as an enlarged threaded head at one end for mounting the operative probe. The tubular body portion of the known probes have been circular in cross section and may be either cylindrical or slightly tapered from the mounting head to the operative tip. While such operative probes have been widely used, they are not entirely satisfactory for certain surgical procedures. For example, in removing a cataract lens from the eye it is necessary for the surgeon to make a small incision near the edge of the cornea to insert the operative probe and surrounding sheath into the eye to engage and emulsify the cataract lens with the distal end of the probe. Operative probes used for this purpose generally are tapered very slightly toward its distal or operative tip where the diameter may be approximately 0.043 and the end beveled, i.e., have an end surface in a plane which is inclined with respect to the longitudinal axis of the body. Depending on the physician's preference, the angle of the end bevel may vary, with 15, 30 and 45 degree bevels being commercially produced.

Inserting a round probe and sheath through the thin wound in the cornea spreads the margins of the wound and tends to induce wound gap which permits fluid leakage from within the eye. Stretching the wound also results in tighter contact between the cornea and the sheath surface and it is believed this tight contact may be a factor in inducing corneal burns which sometimes occur during eye surgery with these instruments.

Use of a round, beveled probe to sculp nuclear material from the anterior surfaces of the lens nucleus results in the material being removed in shallow furrows. The width of the furrows, and consequently the volume of aspirated nucleus, is limited by the diameter of the probe. Increasing the diameter of the probe would produce a corresponding increase in the furrow width but for various reasons it is desirable to maintain the size of the probe as small as is practical.

SUMMARY OF THE INVENTION

It is the primary object of the present invention to provide an ultrasonic surgical instrument which avoids the deficiencies of the prior art devices discussed above and which enables a more efficient, effective and safe use of the instrument for surgical procedure. In accordance with the invention, an improved operative probe is provided for use on conventional ultrasonic handpieces or aspirators which, when inserted into a thin surgical wound, reduces stretching of the margin on the wound while at the same time provides a more uniform fluid-tight contact between the margins of the wound and the surface of the instrument. This is accomplished by shaping the body of the operative probe so as to have a generally elliptical or oval cross sectional shape and employing a shield for the probe which either has a similar cross section shape or is formed from a thin material having sufficient resilience to adopt the desired shape when inserted into a close-fitting wound whereby the wound fits in a more physiological fashion, producing less wound gap and decreasing the stretching of the wound margin.

The oval configuration also reduces the chances of tissue burns as a result of contact of the margins of the wound with an ultrasonically vibrating surface and results in a more fluid-tight contact between the instrument surface and the margin of the wound. As a consequence, when the instrument is used for removing a cataract lens, there is less likelihood of leakage around the instrument, thereby holding the anterior chamber fluid within the eye and maintaining the eye's volumetric integrity. The oval or generally elliptical cross sectional configuration of the operative probe also results in a wider tip which consequently will make a wider furrow when used to sculp the anterior portion of the nucleus. This enables a more rapid removal of material and a consequent reduction in the number of passes which the tip must make, thereby reducing the overall exposure to ultrasonic vibrations during removal of the lens. Clinical tests have shown that the change of probe geometry enables a reduction in time required to remove a cataract lens by approximately 20% which, again, reduces the chances of corneal burn.

DESCRIPTION OF THE DRAWINGS

Other features and advantages of the invention will be apparent from the detailed description contained hereinbelow, taken in conjunction with the drawings, in which:

FIG. 3 is a sectional view taken on line 3—3 of FIG. 2;

FIG. 4 is a sectional view taken on line 4—4 of FIG. 2;

FIG. 5 is a sectional view taken on line 5—5 of FIG. 2 and;

FIG. 6 is a pictorial representation of a human eye in enlarged form and illustrating the use of the apparatus shown in FIGS. 1-6 for cataract removal.

DESCRIPTION OF THE PREFERRED EMBODIMENTS

Figure 1:
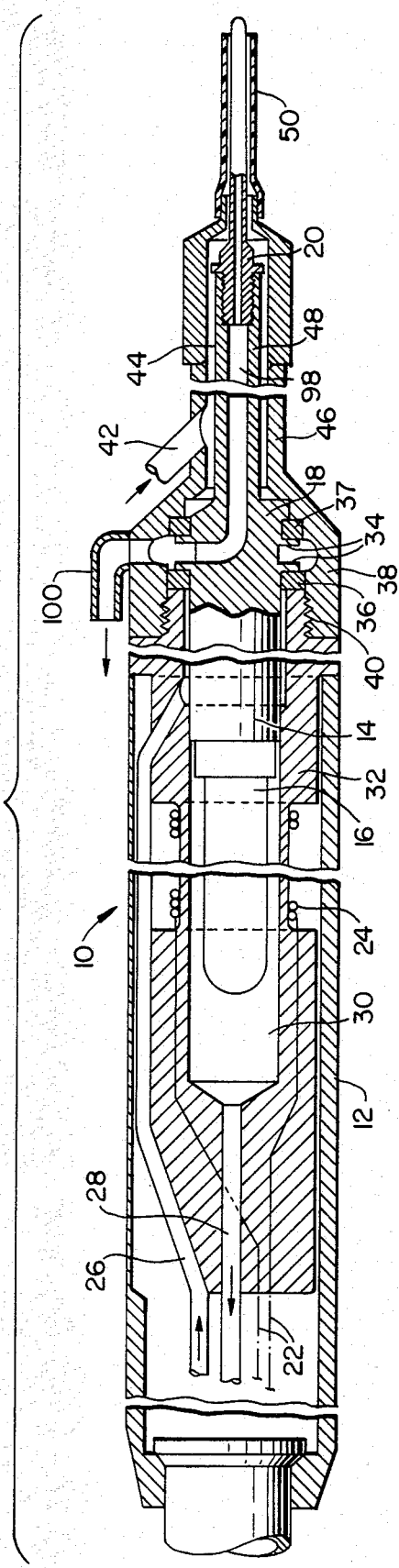
FIG. 1 is a longitudinal sectional view, with portions broken away, of an ultrasonic surgical instrument embodying the present invention.

Referring now to the drawings in detail, FIG. 1 shows an ultrasonic aspirator of the type illustrated, for example, in U.S. Pat. No. 3,693,613 and which is widely used in surgical practice. The ultrasonic aspirator is indicated generally by the reference numeral 10 and includes a handpiece or housing structure 12 enclosing and supporting a vibratory body 14 including a piezoelectric or magnetostrictive transducer 16 and a transmitting element 18 having an operative probe 20 mounted on its distal end in outwardly spaced relation to the housing. Electrical energy is provided from a suitable high-frequency source through conductors 22 to the coil 24 which surrounds and excites the transducer 16. Inlet and outlet conduits 26, 28, respectively, supply a circulating cooling fluid within the handpiece for removing excess heat. The vibrating body assembly is mounted within a cavity 30 of support element 32 which, in turn, is mounted on the end of and projects into the housing 12. A pair of radially extending, axially spaced flanges 34 and a pair of resilient O-ring gasket members 36, 37 effectively isolate the handpiece from vibrations induced by the transducer 16.

An irrigation and aspiration fluid housing 38 is mounted on the end of support element 32 as by a threaded connection 40 and retains the resilient gasket member firmly in position. A fluid inlet housing 42 communicates with the cylindrical fluid chamber 44 between the hollow cylindrical body portion 46 of the housing 38 and the outer surface of an elongated tubular portion 48 of the transmitting body 18. The O-ring seal member 37 provides a fluid seal between member 46 and transmitting body 18 to prevent the flow of irrigation fluid toward the handpiece. A removable sleeve member 50 is mounted on the distal end of body portion 46 of housing 38 and extends in surrounding relation to the elongated operative probe 20. Sleeve member 50, which will be described more fully hereinbelow, acts both as a shield for the axially vibrating operative probe and as a conduit for irrigation fluid from chamber 44 to a position adjacent the operative tip 52 of the probe 20.

The apparatus thus far described is of conventional construction and is commercially available and widely used. The construction and operation of the apparatus according to the present invention may be substantially identical to that described except for the configuration of the operative probe and the removable shield member which surrounds the probe throughout a substantial portion of its length, which features enable a faster, more efficient and safer use of the apparatus for certain surgical procedures including cataract removal.

Referring now to FIGS. 2 through 6, the operative probe 20 includes a base 54 having external threads formed thereon adapted to be received in cooperating female threads on the open distal end of tubular extension 48 of the transmitting element 18. A radially extending flange 56 on base 54 is adapted to seat against the end surface of extension 48. On the side of flange 56 opposite the mounting threads, the base 54 has at least two and preferably four flattened surfaces 58 for engagement by a suitable wrench or other tool for installing and removing the operative probe. A transition portion 60 extends from the flattened end surfaces 58 and is tapered to a short cylindrical neck portion 62 which then is flared into the elongated slender body portion 64 which, as best seen in FIGS. 4 and 6, is substantially elliptical, or oval, in cross section. The probe 20 has a concentric, generally elliptical opening 66 extending through its body, with an axial counterbore 68 extending into the base 54 and communicating with the opening 66. As used herein, the terms "oval" and "elliptical" or "generally elliptical" are interchangable as it is not considered essential that a precise elliptical configuration be used.

The elongated oval-shaped operative body portion 64 of probe 20 may be of substantially uniform wall thickness throughout its length but preferably the outer surface is tapered slightly toward the free end or operative tip 52. For example, in an operative probe which has been successfully used for clinical evaluation in cataract surgery the opening 66 was of uniform cross section throughout the length of body portion 64, with the outer surface tapering to provide a smaller wall thickness at the operative tip 52 than at the end adjacent the cylindrical neck portion 62.

Figure 2:
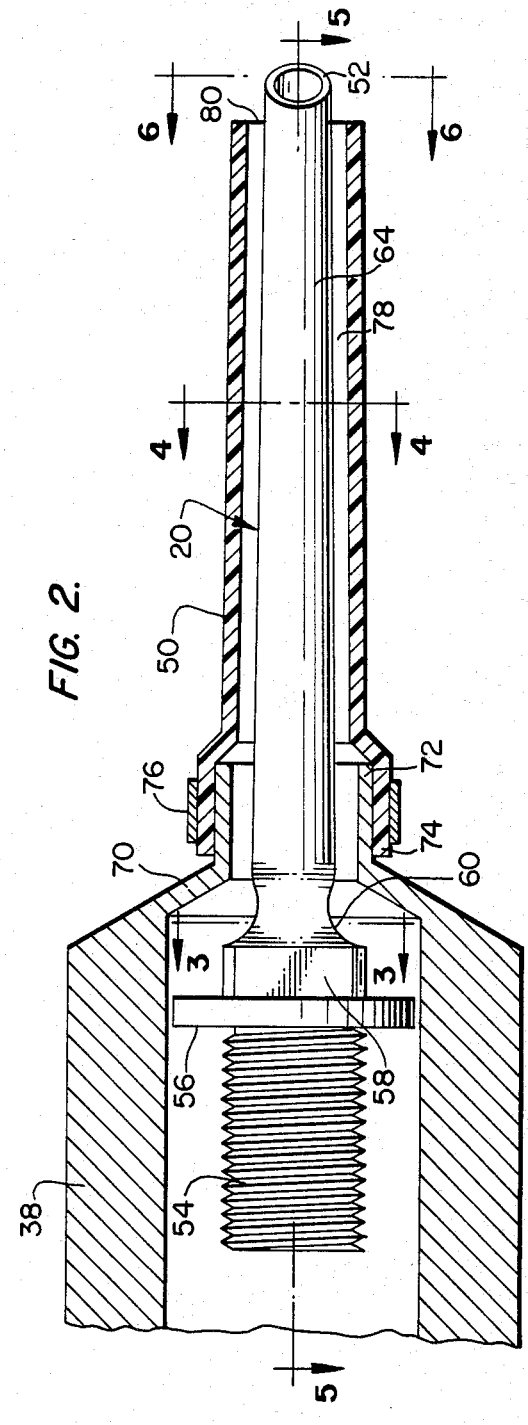
FIG. 2 is an enlarged elevation view of an operative probe employed on the apparatus shown in FIG. 1.

As most clearly seen in FIG. 2, the fluid housing 38 is necked down as at 70 and terminates in a reduced diameter, thin-walled nipple portion 72 which extends in outwardly spaced coaxial relation to the elongated body 64 of probe 20. In FIG. 2, sleeve 50 is illustrated as having an enlarged, circular mounting portion 74 at one end which is telescopingly received on the nipple portion 72 of fluid housing 38, and frictionally retained thereon by a resilient clip member 76. From the enlarged mounting portion 74, sleeve 50 extends in spaced relation to the elongated slender portion 64 of probe 20 to define an irrigation fluid channel 78 between the inner surface of the sleeve and the outer surface of the probe so that irrigating fluid is discharged from the open end 80 of shield 50 in close proximity and surrounding relation to the operative tip 52 of the probe. This surrounding stream of irrigating fluid also acts as a vibration damping element and cooling medium as in the prior art.

Sleeve 50 is preferably formed from a synthetic resin material having a very smooth, low-friction surface. In the embodiment illustrated in the drawing, the sleeve is formed in an oval or substantially elliptical cross sectional configuration corresponding generally to the cross sectional configuration of the elongated slender portion 64 of probe 20 to thereby provide a substantially uniform fluid channel around the periphery of the probe. In this configuration, the sleeve is formed from a thin synthetic resin material which nevertheless has sufficient rigidity to substantially retain its initial oval configuration. In an alternate embodiment, the sleeve is formed from a more resilient silicone rubber material and initially has a substantially circular cross section throughout its length. In this alternate embodiment, when the instrument is inserted into a wound to position the tip 52 at the operative site, the slight pressure from the wound will cause the sleeve to assume a configuration substantially corresponding to the configuration of the elongated slender body 64, with the flow of irrigating fluid along the fluid channel 78 tending to maintain a slight spacing between the inner surface of the sleeve and the outer surface of the probe body around its entire periphery. Although the sleeve is formed from a very thin, resilient material and is therefore easily deformed to the slightly oblong or elliptical configuration, its resistance to compression is such as to prevent peripheral pressure from a wound collapsing the sleeve around the surface of the probe to present an obstruction to flow of the irrigation fluid.

Other configurations of the sleeve may also be used. For example, the sleeve may have a more rigid mounting end adapted to be retained on the housing by friction, or a threaded mounting might be used.

As previously indicated, the invention can be used in the removal of material from essentially any enclosed operative site but is particularly useful in the removal of a cataract lens from the human eye. The use of the apparatus for such lensectomy is illustrated schematically in FIG. 7 which includes a simplified diagram of the human eye to illustrate the manner in which the device is employed. In FIG. 7, the eye is designated generally by the reference numeral 82 with the cataract lens which is to be removed being designated by the number 84. Lens 84 is contained in a membrane including an outer portion 86 known as the anterior capsule. The iris is designated by the reference numeral 88 and the major gel-filled portion of the eye, or vitreous, is designated by the reference numeral 90. A membrane 91 retains the vitreous in the posterior segment of the eye. The cornea, or transparent outer surface of the eye, is shown at 92, and the portion of the eye generally called the anterior chamber is designated as 94.

To use the apparatus of the present invention in a lensectomy, a small incision 96 is made near the edge portion of the cornea 92 to enable the operative probe 20 and shield 50 to be inserted to bring the operative tip 52 into contact with the lens. In this position, ultrasonic energy in the form of longitudinal vibrations transmitted through the probe to the operative tip 52 will break up and emulsify the cataract lens. The emulsified tissue is removed by irrigating fluid which flows through the channel 78 and is returned through the bore 66 of the probe by suction applied through a channel or bore 98 in transmitting body 18 from a fluid outlet conduit 100 connected in fluid housing 38. O-ring seals 36, 37 seal the suction path between the transmitting body and the fluid housing as seen in FIG. 4.

In performing a lensectomy, the surgeon conventionally manipulates the ultrasonic aspirator so as to make a plurality of passes of the operative tip of the vibrating probe over the cataract lens, removing material in a series of shallow furrows. Use of the oval probe according to this invention provides a wider operative tip 52 which results in the removal of the tissue in wider furrows with each pass of the instrument without increasing the overall size of the instrument or necessitating a larger wound for inserting the instrument.

Clinical investigations of operative probes embodying the generally elliptical cross section have established that improved results may be obtained with elliptical configurations wherein the major diameter is only slightly greater than the minor diameter. This improvement is less pronounced however when the major diameter is less than about 1.2 times the minor diameter and for general use in a lensectomy, it is preferred that the major diameter be at least about 1.4 times the minor diameter. Substantiably greater major diameter to minor diameter ratios may be preferred for some procedures. The elliptical configuration of the operative tip has been found to fit the wound in a more physiological fashion in that its shape is more similar to that made by a kerotome or other appropriate surgical instrument. This results in less wound gap when the instrument is inserted, with a consequent decrease in stretching of the wound and reduction in the chances of corneal burn. The close fit between the oval or elliptical configuration and the wound prevent escape of the anterior chamber fluids around the instrument during a lensectomy, thereby maintaining the eye's volumetric integrity.

The angle $\alpha$ (FIG. 5) of the plane of the open end surface of the operative tip 52, in combination with the oval geometry of the tip, not only produces a highly efficient instrument for emulsifying tissue but also facilitates occlusion of the tip with the nuclear material. This enables the surgeon to more easily and accurately maintain control of the lens position and keep it away from delicate eye structure, thereby greatly enhacing the safety of the operative procedure.

The angle $\alpha$ may vary depending on the operative procedure being performed and upon preference of the individual surgeon, but generally should be within the range of from about 15° to about 75° measured from a plane perpendicular to the longitudinal axis of the probe. For use in a lensectomy, tip angles $\alpha$ within the range of about 15° to 45° may be preferred for nuclear material of average hardness while greater angles may be preferred for nuclear material of different hardness. The plane of the operative tip and the plane containing the longitudinal axis of the probe and the major diameter of the elongated slender oval portion intersect along a major diameter to thereby provide a maximum effective dimenion for the operative tip while at the same time orienting the tip to facilitate occlusion and cotrol lens position.

The increase in tip width, and the consequent wider furrows when used to sculp anterior portions of the nucleus, results in a greater amount of material being removed with each pass of the tip. An important feature of this is the overall reduction in ultrasound exposure time required for removing a lens. Clinical investigations have shown this reduction of time may be approximately 20%. Another advantage of this feature is that it also reduces the time during which the lens can break through the posterior capsule 91.

In the use of the prior art circular probes, followability, the tendency for nuclear material to be engulfed, and the ease of occlusion decrease with an increase in the bevel angle of the operative tip. Surprisingly, however, surgeons who have evaluated the oval tip during removal of cataract lens from the human eye have reported that the elliptical geometry in conjunction with the inclined tip surface often improves nuclear followability and greatly facilitates the ease with which the tip can be occluded even with bevel angles (60) up to about 75°.

Once the nucleus has been engaged with suction, it can be manipulated within the eye. Thus, the elliptical geometry of the probe having a relatively high bevel angle on the tip, for example a 45° bevel, has been found to emulsify more quickly, induce less trauma to the surgical wound, improve nuclear manipulation and reduce the overall time required for a lensectomy, thereby increasing the probability of a successful procedure for the patient.

While preferred embodiments have been disclosed and described, it should be understood that the invention is not limited to such embodiments but rather that it is intended to include all embodiments which would be apparent to one skilled in the art and which come within the spirit and scope of the invention.

What is claimed is:

1. In an ultrasonic surgical aspirator for breaking apart and removing tissue from an operative site recessed within a body, the aspirator including a transducer for converting high-frequency electrical energy to mechanical vibrations, an elongated vibration transmitting body having one end operably associated with the transducer and its other end adapted to threadably receive and support an operative probe, and a housing for supporting the transmitting body and the transducer and providing an inlet and outlet for irrigation fluid to be circulated over the operative site, the improvement wherein said operative probe comprises,
    a threaded mounting base portion adapted to be threadably mounted onto said transmitting body and an elongated slender body portion means having a longitudinal axis adapted to be inserted into a tissue body, said elongated portion terminating in an open end having free end surface means defining an operative tip for engaging and breaking apart tissue at the recessed operative site,
    an axial opening extending through said probe to enable the removal of broken-up tissue from the operative site through the probe,
    said free end surface means extending in a plane disposed at an acute angle relative to the longitudinal axis of the slender body portion,
    said slender body portion means having a substantially elliptical cross section defining a major axis and a minor axis from said free end surface means throughout at least a major portion of its length, and vibrating along said longitudinal axis, and
    a plane containing the longitudinal axis of the slender body portion means and the major axis of the substantially elliptical cross section thereof intersecting the plane of said free end surface means along the major axis of the oval or elliptical open end at said tip, wherein ultrasonic cutting time is reduced by the removal of said tissue in furrows corresponding in width to the major axis of said free end surface means and wherein wound spreading is reduced along the minor axis of said free end surface means of the slender body portion means.

2. The invention according to claim 1 wherein the plane of said free end surface extends at an angle within the range of about 15° to about 75° from a plane perpendicular to the longitudinal axis of said probe.

3. The invention according to claim 1 wherein the plane of said free end surface extends at an angle within the range of about 15° to about 45° from a plane perpendicular to the longitudinal axis of said probe.

4. The invention according to claim 1 wherein the major axis of said substantially elliptical slender body portion is at least about 1.2 times its minor axis.

5. The invention according to claim 1 wherein the major axis of said substantially elliptical slender body portion means is at least about 1.4 times its minor axis.

6. The invention according to claim 1 wherein the outer surface of said slender body portion means is tapered slightly from a maximum dimension adjacent said base to a minimum dimension adjacent said operative tip.

7. The invention according to claim 1 further comprising an elongated tubular sleeve member having one end supported on said housing, said sleeve member extending in outwardly spaced substantially concentric relation to said slender body portion means throughout a substantial portion of its length and terminating in an open end in spaced relation to said operative tip, said sleeve in use having a substantially elliptical cross sectional configuration generally corresponding to the substantially elliptical cross section of said slender body portion at least along a portion of its length.

8. The invention according to claim 7 wherein said sleeve member is formed from a thin resilient silicone rubber material and is initially substantially circular in cross section throughout its length, said resilient silicone rubber material being deformable by slight pressure from the tissue body to substantially conform the resilient sleeve to the substantially elliptical configuration of the slender body portion means when the sleeve and operative probe are inserted into a tissue body to position the operative tip at the operative site.

9. The invention according to claim 5 wherein said one end of said sleeve is circular in cross section and is adapted to be telescopingly received on a cylindrical portion of said housing, said sleeve being substantially rigid and being substantially elliptical throughout a major portion of its length from said circular end portion to its open end.

10. The invention according to claim 1 wherein the plane of said free end surface extends at an acute angle of at least about 15° from a plane perpendicular to the longitudinal axis of said probe, and wherein the major axis of said substantially elliptical slender body portion means is at least about 1.2 times its minor axis.

11. The invention according to claim 10 wherein the outer surface of said slender body portion means is tapered slightly from a maximum dimension adjacent said base to a minimum dimension adjacent said operative tip.

12. The invention according to claim 10 further comprising an elongated tubular sleeve member having one end supported on said housing, said sleeve member extending in outwardly spaced substantially concentric relation to said slender body portion means throughout a substantial portion of its length and terminating in an open end in spaced relation to said operative tip, said sleeve in use having a substantially elliptical cross sectional configuration generally corresponding to the substantially elliptical cross section of said slender body portion at least along a portion of its length.

13. The invention according to claim 12 wherein said sleeve member is formed from a thin resilient silicone rubber material and is initially substantially circular in cross section throughout its length, said resilient silicone rubber material being deformable by slight pressure from the tissue body to substantially conform the resilient sleeve to the substantially elliptical configuration of the slender body when the sleeve and operative probe are inserted into a tissue body to position the operative tip at the operative site.

14. The invention according to claim 12 wherein said one end of said sleeve is circular in cross section and is adapted to be telescopingly received on a cylindrical portion of said housing, said sleeve being substantially rigid and being substantially elliptical throughout a major portion of its length from said circular end portion to its open end.

15. A method of performing a lensectomy on a human eye using an ultrasonic surgical aspirator having an elliptically-shaped probe for breaking apart and removing the lens from the eye in a series of furrows having contours corresponding to the elliptically-shaped probe, said method comprising:

providing on said surgical aspirator an operative probe having an elongated slender body portion having a substantially elliptical cross section and having a free end surface defining an operative tip disposed in a plane extending at an angle within the range of about 15° to about 75° from a plane perpendicular to the longitudinal axis of the operative probe, with a plane containing the longitudinal axis and the major axes of the elongated slender body portion intersecting the plane of the free end surface along the major axis of the substantially elliptical slender body portion at the open end, inserting the operative probe of the ultrasonic surgical aspirator through an incision in the cornea of the eye and positioning said operative tip adjacent the lens to be removed, energizing the ultrasonic surgical aspirator to deliver ultrasonic vibrations through the probe to break up the lens tissue, and manipulating the ultrasonic aspirator to move the operative tip thereof over the lens tissue in a series of passes in a direction substantially perpendicular to the major axis of the substantially elliptical opening in the operative tip of the probe, to form a furrow having a contour corresponding to the elliptical shaped probe, and repeating the manipulative step while flowing irrigation fluid along the outer surface of the operative probe; and removing the fluid through the open center of the elliptical probe until the lens is completely removed.

* * * * *